(12) United States Patent
Xu et al.

(10) Patent No.: US 9,029,611 B2
(45) Date of Patent: May 12, 2015

(54) DEHYDROGENATION OF CYCLOHEXANONE TO PRODUCE PHENOL

(75) Inventors: Teng Xu, Houston, TX (US); Jihad M. Dakka, Whitehouse Station, NJ (US); Christopher L. Becker, Manhattan, KS (US); Keith H. Kuechler, Friendswood, TX (US); Francisco M. Benitez, Cypress, TX (US); Charles M. Smith, Houston, TX (US); Hari Nair, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 132 days.

(21) Appl. No.: 13/512,796

(22) PCT Filed: Dec. 17, 2010

(86) PCT No.: PCT/US2010/060989
§ 371 (c)(1),
(2), (4) Date: Jul. 20, 2012

(87) PCT Pub. No.: WO2011/096989
PCT Pub. Date: Aug. 11, 2011

(65) Prior Publication Data
US 2012/0323045 A1    Dec. 20, 2012

Related U.S. Application Data

(60) Provisional application No. 61/301,786, filed on Feb. 5, 2010, provisional application No. 61/358,711, filed on Jun. 25, 2010.

(30) Foreign Application Priority Data

Aug. 5, 2010    (EP) ..................................... 10171955

(51) Int. Cl.
| | | |
|---|---|---|
| C07C 37/06 | (2006.01) | |
| C07C 2/74 | (2006.01) | |
| C07C 37/07 | (2006.01) | |
| C07C 37/08 | (2006.01) | |
| C07C 45/53 | (2006.01) | |
| C07C 407/00 | (2006.01) | |

(52) U.S. Cl.
CPC . *C07C 2/74* (2013.01); *C07C 37/07* (2013.01); *C07C 37/08* (2013.01); *C07C 45/53* (2013.01); *C07C 407/00* (2013.01); *C07C 2101/14* (2013.01); *C07C 2529/70* (2013.01); *C07C 2529/74* (2013.01)

(58) Field of Classification Search
USPC ................... 568/772, 799, 806, 300
See application file for complete search history.

(56) References Cited

U.S. PATENT DOCUMENTS

| | | | | |
|---|---|---|---|---|
| 3,534,110 A | * | 10/1970 | Page et al. .................... | 568/799 |
| 3,580,970 A | | 5/1971 | Swift | |
| 4,139,570 A | * | 2/1979 | Antos ........................... | 585/434 |
| 4,439,409 A | | 3/1984 | Puppe et al. | |
| 4,826,667 A | | 5/1989 | Zones et al. | |
| 4,933,507 A | | 6/1990 | Inoki et al. | |
| 4,954,325 A | | 9/1990 | Rubin et al. | |
| 5,232,580 A | * | 8/1993 | Le et al. ......................... | 208/114 |
| 5,236,575 A | | 8/1993 | Bennett et al. | |
| 5,250,277 A | | 10/1993 | Kresge et al. | |
| 5,362,697 A | | 11/1994 | Fung et al. | |
| 6,014,018 A | | 1/2000 | Wu et al. | |
| 6,037,513 A | | 3/2000 | Chang et al. | |
| 6,077,498 A | | 6/2000 | Diaz Cabañas et al. | |
| 6,201,157 B1 | | 3/2001 | Keenan | |
| 6,720,462 B2 | | 4/2004 | Kuhnle et al. | |
| 6,756,030 B1 | | 6/2004 | Rohde et al. | |
| 7,285,685 B2 | | 10/2007 | Walsdorff et al. | |
| 7,579,511 B1 | * | 8/2009 | Dakka et al. ................... | 585/316 |
| 7,605,107 B2 | * | 10/2009 | Soled et al. .................... | 502/216 |
| 8,487,140 B2 | * | 7/2013 | Buchanan et al. ............. | 568/799 |
| 2012/0302798 A1 | | 11/2012 | Dakka et al. | |
| 2012/0302799 A1 | | 11/2012 | Dakka et al. | |
| 2012/0316365 A1 | | 12/2012 | Xu et al. | |
| 2012/0323046 A1 | | 12/2012 | Xu et al. | |
| 2013/0090499 A1 | | 4/2013 | Xu et al. | |
| 2014/0066663 A1 | | 3/2014 | Dakka et al. | |
| 2014/0148620 A1 | | 5/2014 | Xu et al. | |

FOREIGN PATENT DOCUMENTS

| | | |
|---|---|---|
| EP | 0 293 032 | 11/1988 |
| GB | 640363 | 4/1948 |
| JP | 07-188082 | 7/1995 |
| WO | WO 97/17290 | 5/1997 |
| WO | WO 2009/025939 | 2/2009 |
| WO | WO 2009/102517 | 8/2009 |
| WO | WO 2009/134514 | 11/2009 |
| WO | WO 2010/024975 | 3/2010 |

* cited by examiner

*Primary Examiner* — Sudhakar Katakam
*Assistant Examiner* — Pancham Bakshi

(57) ABSTRACT

In a process for the dehydrogenation of cyclohexanone to produce phenol, a feed comprising cyclohexanone is contacted with a dehydrogenation catalyst under dehydrogenation conditions comprising a temperature of less than 400° C. and a pressure of less than 690 kPa, gauge, such 0.1 to 50 wt % of the cyclohexanone in said feed is converted to phenol and the dehydrogenation product contains less than 100 ppm by weight of alkylbenzenes.

23 Claims, No Drawings

DEHYDROGENATION OF CYCLOHEXANONE TO PRODUCE PHENOL

PRIORITY CLAIM

This application is a National Stage Application of International Application No. PCT/US2010/060989 filed Dec. 17, 2010, which claims priority to U.S. Application Ser. No. 61/301,786, filed Feb. 5, 2010, U.S. Application Ser. No. 61/358,711, filed Jun. 25, 2010, and EP Application Serial No. 10171955.7, filed Aug. 5, 2010, all of which are incorporated herein by reference in their entirety.

CROSS REFERENCE TO RELATED APPLICATIONS

This application is related to U.S. Publication No. WO2009/134514, published Nov. 5, 2009; U.S. Publication No. WO2010/024975, published Mar. 4, 2010; U.S. Application Ser. No. 61/301,780, filed Feb. 5, 2010; U.S. Application No. 61/301,786, filed Feb. 5, 2010; U.S. Application No. 61/301,794, filed Feb. 5, 2010; U.S. Application No. 61/301,799, filed Feb. 5, 2010; U.S. Application No. 61/391,832, filed Oct. 11, 2010; U.S. Application No. 61/424,242 filed Dec. 17, 2010; and International Publication No. WO2011/096990, published Aug. 11, 2011.

FIELD

The present invention relates to a process for the dehydrogenation of cyclohexanone to produce phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, due to a developing shortage, the cost of propylene is likely to increase. Thus, a process that uses higher alkenes instead of propylene as feed and coproduces higher ketones, rather than acetone, may be an attractive alternative route to the production of phenols.

One such process involves the hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts. Such a process is described in, for example, U.S. Pat. No. 6,037,513.

However, one problem in producing phenol by way of the cleavage of cyclohexylbenzene hydroperoxide is that the cyclohexanone and phenol produce an azeotropic mixture composed of 28 wt % cyclohexanone and 72 wt % phenol. Thus any attempt to separate the cleavage effluent by simple distillation results in this azeotropic mixture. To obviate this problem it has been proposed to integrate the cyclohexylbenzene oxidation and cleavage process with a dehydrogenation step whereby at least part of the cyclohexanone is converted to additional phenol (see International Patent Publication No. WO2010/024975). Such a dehydrogenation step is generally achieved by contacting the cyclohexanone with a supported noble metal catalyst at a temperature of about 250° C. to about 500° C.

For example, U.S. Pat. No. 3,534,110 discloses a process for the catalytic dehydrogenation of cyclohexanone and/or cyclohexanol to phenol over a catalyst comprising platinum and preferably iridium on a silica support. The catalyst also contains 0.5 to 3 wt % of an alkali or alkaline earth metal compound, which, according to column 3, lines 43 to 49, should be incorporated after addition of the platinum since otherwise the resulting catalyst composition has inferior activity, selectivity and life. To obtain high conversion rates, the '110 patent teaches that the dehydrogenation should be conducted at a temperature of 320 to 450° C. and a pressure of 0.5 to 10 kg/cm$^2$.

In addition, U.S. Pat. No. 3,580,970 discloses a process for the dehydrogenation of cycloaliphatic alcohols and ketones to the corresponding hydroxyaromatic alcohols in the presence of a catalyst comprising a Group VIII metal, particularly nickel, and tin in a molar amount of about 1.7 to about 15 moles of Group VIII metal per mole of tin. The catalyst may further comprise an alkali metal stabilizing agent in an amount between about 0.3 to about 10 parts by weight of an alkali metal sulfate per part by weight of the Group VIII metal. The hydrogenation can be conducted at 200 to 500° C., but conversion is said to suffer if the temperature is allowed to decrease below the preferred range of 300 to 450° C.

U.S. Pat. No. 4,933,507 discloses a method of dehydrogenating cyclohexenone to phenol comprising reacting hydrogen and cyclohexenone in the vapor phase in a molar ratio of 0.5 to 4.0 moles of hydrogen per mole of cyclohexenone at a pressure of at least one atmosphere and a reaction temperature of 300° C. to 500° C. using a solid phase catalyst containing platinum, in the range of 0.2 to 10 wt % of the sum of the catalyst plus support, and an alkali metal, in the range of 0.2 to 3.0 calculated in terms of the weight ratio of $K_2CO_3$ to platinum, both the platinum and the alkali metal being carried on a support.

U.S. Pat. No. 7,285,685 discloses a process for the dehydrogenation of a saturated carbonyl compound, such as cyclohexanone, in the gas phase over a heterogeneous dehydrogenation catalyst comprising platinum and/or palladium and tin on an oxidic support, such as zirconium dioxide and/or silicon dioxide. In general, the dehydrogenation catalyst contains from 0.01 to 2 wt %, preferably from 0.1 to 1 wt %, particularly preferably from 0.2 to 0.6 wt %, of palladium and/or platinum and from 0.01 to 10 wt %, preferably from 0.2 to 2 wt %, particularly preferably from 0.4 to 1 wt %, of tin, based on the total weight of the dehydrogenation catalyst. In addition, the dehydrogenation catalyst can further comprise one or more elements of Groups I and/or II, preferably potassium and/or cesium, in an amount of from 0 to 20 wt %, preferably from 0.1 to 10 wt %, particularly preferably from 0.2 to 1.0 wt %, based on the total weight of the catalyst. The temperature employed in the dehydrogenation process can range from 300 to 1200° C., preferably from 400 to 600° C.

Research into the cyclohexanone dehydrogenation process has now shown that, although catalyst optimization can allow the production of phenol with good selectivity, typical process conditions result in the coproduction of significant levels of impurities. These impurities include alkylbenzenes, such as t-butylbenzene and n-pentylbenzene, and alkylphenols, such as 2-methyl phenol, as well as heavy products, such as 2-phenyl phenol, diphenyl ether, dibenzofuran and cyclohexyl phenyl ether. Whereas the heavy products result in undesirable yield loss, the alkylbenzenes and alkylphenols pose particular problems since they typically co-boil with or form azeotropic mixtures with phenol. This renders purification of the phenol extremely difficult and expensive. According to the present invention, it has now been found that, by operating the dehydrogenation process at sufficiently mild conditions to lower the cyclohexanone conversion levels to below 50%, the production of impurities and especially alkylbenzenes and alkylphenols can be reduced to levels tolerable in the phenol product.

SUMMARY

In one aspect, the invention resides in a process for the dehydrogenation of cyclohexanone to produce phenol, the process comprising contacting a feed comprising cyclohexanone with a dehydrogenation catalyst under dehydrogenation conditions comprising a temperature of less than 400° C. and a pressure of less than 100 psig (690 kPa, gauge) such that 0.1 to 50 wt % of the cyclohexanone in said feed is converted to phenol and the dehydrogenation product contains less than 100 ppm by weight of alkylbenzenes and alkylphenols.

Conveniently, the dehydrogenation conditions comprise a temperature of about 250° C. to about 375° C. and a pressure about 0 to about 50 psig (450 kPa, gauge).

Conveniently, from about 15 to about 45 wt % of the cyclohexanone in said feed is converted to phenol.

Conveniently, the dehydrogenation product contains less than 75 ppm, such as less than 50 ppm, by weight of alkylbenzenes and alkylphenols.

In one embodiment, the feed also comprises a diluent substantially inert under said dehydrogenation conditions. Conveniently, the weight ratio of diluent to cyclohexanone in said feed is from about 1:100 to about 10:1. Typically, the diluent comprises a phenol or a hydrocarbon, such as at least one of cyclohexane and benzene.

In one embodiment, the dehydrogenation catalyst comprises (i) a support, such as silica, a silicate, and/or an aluminosilicate; (ii) a dehydrogenation component comprising at least one metal or compound thereof selected from Groups 6 to 10 of the Periodic Table of Elements, such as platinum and/or palladium; and (iii) potassium or a potassium compound. Conveniently, the potassium or potassium compound is present in an amount of about 0.1 to about 5 wt % of potassium based upon the total weight of the dehydrogenation catalyst.

In a further aspect, the invention resides in a process for producing phenol from benzene, the process comprising:

(a) reacting benzene and hydrogen with a hydroalkylation catalyst under hydroalkylation conditions to produce cyclohexylbenzene;

(b) oxidizing cyclohexylbenzene from (a) to produce cyclohexylbenzene hydroperoxide;

(c) converting cyclohexylbenzene hydroperoxide from (b) to produce an effluent steam comprising phenol and cyclohexanone; and (d) contacting at least a portion of the cyclohexanone from (c) with a dehydrogenation catalyst under dehydrogenation conditions comprising a temperature of less than 400° C. and a pressure of less than 100 psig (690 kPa, gauge) such that 0.1 to 50 wt % of the cyclohexanone is converted to phenol and the dehydrogenation product contains less than 100 ppm by weight of alkylbenzenes and alkylphenols.

DETAILED DESCRIPTION

Described herein is a process for producing phenol by the dehydrogenation of cyclohexanone. More particularly, there is described an integrated process for producing phenol from benzene, in which the benzene is converted to cyclohexylbenzene, which is then oxidized and cleaved to produce phenol and cyclohexanone, and at least part of the cyclohexanone in the resultant product is then deydrogenated to generate additional phenol. In the present process, the dehydrogenation conditions are controlled so as to reduce the level of alkylbenzenes and alkylphenols in the phenol product to sufficiently low levels that their presence in the product can be tolerated thereby avoiding the need for expensive separation regimes.

Production of Cyclohexylbenzene

The first step in the present integrated process for producing phenol comprises conversion of benzene to cyclohexylbenzene. This can be achieved by any known technique, including direct alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting benzene with hydrogen under hydroalkylation conditions in the presence of a hydroalkylation catalyst whereby the benzene undergoes the following reaction (1) to produce cyclohexylbenzene (CHB):

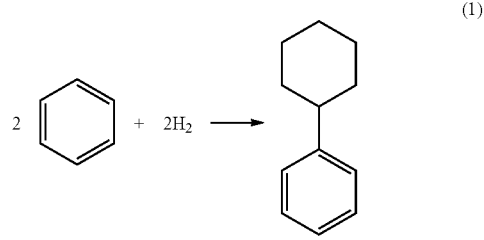 [SMILES: c1ccccc1 ; c1ccc(C2CCCCC2)cc1]

(1)

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur or CO and less than 10 ppm, such as less than 1 ppm, for example less than 0.1 ppm, nitrogen.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, borosilicate, or gallosilicate, the amount of hydrogenation metal present is such that the molar ratio of the aluminum, boron, gallium in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain some dialkylated products, as well as unreacted aromatic feed and the desired monoalkylated species. The unreacted aromatic feed is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 hr$^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 to 500 psig (200 to 3550 kPa, guage) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof. Generally, the acid catalyst includes at least one aluminosilicate, aluminophosphate or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least part of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 500 psig (100 to 3550 kPa, guage), a weight hourly space velocity of about 0.2 to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

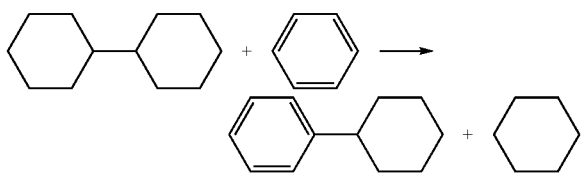

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

At least a portion of the oxidation reaction effluent is subjected to a cleavage reaction to convert the cyclohexyl-1-phenyl-1-hydroperoxide to phenol and cyclohexanone. Cleavage may be conducted on oxidation reaction effluent, with or without the effluent undergoing any prior separation or treatment. For example, all or a fraction of the oxidation reaction effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Application No. WO 2009/025939.

Hydroperoxide Cleavage

The final reactive step in the conversion of the cyclohexylbenzene into phenol and cyclohexanone involves the acid-catalyzed cleavage of the cyclohexyl-1-phenyl-1-hydroperoxide produced in the oxidation step.

Generally, the acid catalyst used in the cleavage reaction is at least partially soluble in the cleavage reaction mixture, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage reaction mixture contains at least 50 weight-parts-per-million (wppm) and no greater than 5000 wppm of the acid catalyst, or at least 100 wppm to and to no greater than 3000 wppm, or at least 150 wppm to and no greater than 2000 wppm of the acid catalyst, or at least 300 wppm and no greater than 1500 wppm of the acid catalyst, based upon total weight of the cleavage reaction mixture.

In one embodiment, the cleavage reaction mixture contains a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less such as acetone, methylethyl ketone, 2- or 3-pentanone, cyclohexanone, and methylcyclopentanone. The preferred polar solvent is acetone. Generally, the polar solvent is added to the cleavage reaction mixture such that the weight ratio of the polar solvent to the cyclohexylbenzene hydroperoxide in the mixture is in the range of about 1:100 to about 100:1, such as about 1:20 to about 10:1, and the mixture comprises about 10 to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage reaction mixture includes cyclohexylbenzene in an amount of at least 50 wt %, or at least 60 wt %, or at least 65 wt %, or at least 70 wt %, or at least 80 wt %, or at least 90 wt %, based upon total weight of the cleavage reaction mixture.

Suitable cleavage conditions include a temperature of greater than 50° C. and no greater than 200° C., or at least 55° C. and no greater than 120° C., and a pressure of at least 1 and no greater than 370 psig (at least 7 and no greater than 2,550 kPa, gauge), or at least 14.5 and no greater than 145 psig (at least 100 and no greater than 1,000 kPa, gauge) such that the cleavage reaction mixture is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone, each of which generally comprise about 40 to about 60 wt %, or about 45 to about 55 wt % of the cleavage reaction product, such wt % based on the weight of the cleavage reaction product exclusive of unreacted cyclohexylbenzene and acid catalyst.

The cleavage reaction product also typically contains unreacted acid catalyst and hence at least a portion of the cleavage reaction product is normally neutralized with a basic material to remove or reduce the level of acid in the product.

Suitable basic materials include alkali metal hydroxides and oxides, alkali earth metal hydroxides and oxides, such as sodium hydroxide, potassium hydroxide, magnesium hydroxide, calcium hydroxide, calcium oxide and barium hydroxide. Sodium and potassium carbonates may also be used, optionally at elevated temperatures.

In various embodiments, the basic material comprises one or more of: a caustic exchange resin (e.g., sulfonic ion-exchange resin); ammonia or ammonium hydroxide; a basic clay such as limestone, dolomite, magnesite, sepiolite and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium and radium; an oxide of Group III of the Periodic Table of Elements treated with a metal selected from lithium, potassium, sodium, rubidium and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines and alkanolamines. In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth and higher valency oxides; hydrotalcites, calcined hydrotalcites and spinels, specifically hydrotalcites treated with an alkali metal selected from lithium, potassium, sodium, rubidium, cesium, and combinations thereof; perovskites; and beta-aluminas.

In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, a liquid basic material employed a neutralization reaction in the present invention, such as an amine or diamine as has been discussed, has a relatively low volatility, with a normal boiling point temperature above that of cyclohexylbenzene, such that it will tend to remain in the bottoms product in subsequent fractionation operations that may be conducted on the least a portion of the treated cleavage reaction product that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 to about 500 psig (5 kPa to 3450 kPa, gauge), or about 10 to 200 psig (70 to 1380 kPa, gauge) such that the treated cleavage reaction mixture is completely or predominantly in the liquid phase during the neutralization reaction.

After neutralization, the neutralized acid product can be removed from the cleavage product leaving a crude mixture of phenol and cyclohexanone which is then treated to convert at least part of the cyclohexanone to additional phenol.

Cyclohexanone Dehydrogenation

In order to maximize the production of phenol from the benzene starting material, at least part of the cyclohexanone in the cleavage effluent is subjected to dehydrogenation according to the following reaction:

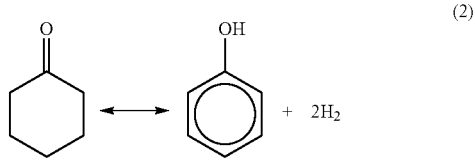

(2)

As stated above, cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. Moreover, although the efficiency of the separation can be enhanced by conducting the distillation under at least partial vacuum, phenol/cyclohexanone separation remains a costly process. Thus, in one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to said dehydrogenation reaction contains less than 50 wt %, for example less than 30 wt %, such as less than 1 wt %, phenol. The separation of phenol is conveniently effected by vacuum and/or extractive distillation. Additional distillation steps can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

The catalyst employed in the cyclohexanone dehydrogenation reaction comprises (i) a support; (ii) a dehydrogenation component comprising at least one metal or compound thereof selected from Groups 6 to 10 of the Periodic Table of Elements; and (iii) potassium or a potassium compound.

The catalyst support is typically formed of silica, a silicate, an aluminosilicate, carbon, or carbon nanotubes. In one embodiment, the support comprises a crystalline, mesoporous silicate material selected from MCM-41, MCM-48 and MCM-50. In other embodiments, the silica support has a surface area as measured by ASTM D3663 in the range from about 10 m$^2$/gram to about 1000 m$^2$/gram, such as from about 20 m$^2$/gram to about 500 m$^2$/gram, a pore volume in the range of from about 0.2 cc/gram to about 3.0 cc/gram and a median pore diameter in the range from about 10 angstroms to about 2000 angstroms, such as from about 20 angstroms to about 500 angstrom. Such pore volume and median pore diameter values are determined by mercury intrusion porosimetry as described in ASTM D4284. The support may or may not comprise a binder.

Generally, the dehydrogenation component comprises at least one metal component selected from Groups 6 to 10 of the Periodic Table of Elements, such as platinum and palladium. Typically, the dehydrogenation component is present in an amount between about 0.1 wt % and about 10 wt % of the catalyst. In one embodiment, the dehydrogenation component is present in an amount between about 0.1 wt % and about 5 wt % of the catalyst or between about 0.2 wt % and about 4 wt % of the catalyst or between about 0.3 wt % and about 3 wt % of the catalyst or between about 0.4 wt % and 2 wt % of the catalyst.

In order to achieve optimal phenol selectivity, together with enhanced stability of the dehydrogenation metal, the dehydrogenation catalyst contains potassium or a potassium compound in an amount of about 0.1 to about 5 wt %, generally about 0.2 to about 2 wt %, of potassium based upon the total weight of the catalyst composition.

It will be understood that the potassium in the catalyst composition may not be purely the elemental metal, but could, for example, be at least partly in another form, such as a salt, oxide, chloride, hydride, sulfide, carbonate, etc. For purposes of this application, the wt % of potassium or potassium compound in the catalyst composition is calculated based upon the amount of potassium (i.e., potassium) used to form the catalyst composition. For purposes of illustration, a catalyst composition made with 5.21 grams of potassium carbonate (3.0 grams of potassium) and 66.87 grams of tetraammine platinum hydroxide solution (4.486 wt % Pt) that is supported on 294 grams of silicon dioxide contains 1 wt % of potassium and 1 wt % Pt, based upon total weight of the catalyst composition.

Moreover, for purposes of determining wt % s of various components, only that portion of the support that supports the dehydrogenation component and/or the potassium or potassium compound shall be considered.

The dehydrogenation catalyst is typically prepared by sequentially or simultaneously treating the support, such as by impregnation, with one or more liquid compositions comprising the dehydrogenation component or a precursor thereof and the potassium component or a precursor thereof in a liquid carrier, such as water. An organic dispersant may be added to each liquid carrier to assist in uniform application of the metal component(s) to the support. Suitable organic dispersants include amino alcohols and amino acids, such as arginine. Generally, the organic dispersant is present in the liquid composition in an amount between about 1 and about 20 wt % of the liquid composition.

In one preferred embodiment, the catalyst is prepared by sequential impregnation with the potassium component being applied to the support before the dehydrogenation component.

After application of each of the dehydrogenation metal and the potassium to the support, the support is preferably heated at a temperature of about 100° C. to about 700° C. for example about 200° C. to about 500° C., such as 300° C. to about 450° C., for a time of about 0.5 to about 50 hours, such as about 1 to about 10 hours. In addition to removing any liquid carrier and dispersant used to apply the metal component to the support, the heating is believed to assist in bonding the metal to the support and thereby improve the stability of the final catalyst. The heating is preferably conducted in an oxidizing atmosphere, such as air, although a reducing atmosphere, such as hydrogen, can also be employed.

In one embodiment, the dehydrogenation catalyst has an oxygen chemisorption value of greater than about 30%, such as greater than about 40%, for example greater than about 50%, even greater than about 60%, greater than about 70%, or even greater than about 80%. As used herein, the oxygen chemisorption value of a particular catalyst is a measure of metal dispersion on the catalyst and is defined as [the ratio of the number of moles of atomic oxygen sorbed by the catalyst to the number of moles of dehydrogenation metal contained by the catalyst]×100%. The oxygen chemisorption values referred to herein are measured using the following technique. Chemisorption measurements are obtained under static high vacuum conditions on a Quantachrome Autosorb 1A instrument. Approximately 0.3-0.5 grams of catalyst are loaded into a quartz cell and dried in flowing He by heating at 4° C./min to 130° C. and holding for 1 hour. The flow is then switched to hydrogen and the catalyst is reduced in flowing hydrogen by heating at 2° C./min to 425° C., holding isothermal for 2 hours, and then cooling to 400° C. in flowing hydrogen. Following reduction, the sample is evacuated (while still at 400° C.) with a turbomolecular pump for 30 minutes to remove any chemisorbed hydrogen. With the sample still under vacuum, the temperature is lowered to 40° C. and held isothermal during subsequent experiments. An 8-point isotherm (with pressures between 80 and 400 torr [11 kPa to 53 kPa]) is measured at 40° C. with $O_2$ as the adsorbent molecule. Extrapolation of the linear portion of this curve to zero pressure gives the total or combined adsorption uptake.

The dehydrogenation process is conducted under relatively mild conditions comprising a temperature of less than 400° C., such as about 250° C. to about 375° C., and a pressure of less than 100 psig (690 kPa, gauge), for example about 0 to about 50 psig (450 kPa, gauge), such that the per pass conversion of cyclohexanone to phenol in the feed is 0.1 to 50 wt %, typically from about 15 to about 45 wt %. By using such mild conditions the amount of undesirable alkylbenzenes and alkylphenols in the dehydrogenation product can be reduced to less than 100 ppm, such as less than 75 ppm, or even less than 25 ppm by weight of the dehydrogenation product. At such low levels, the alkylbenzenes and alkylphenols can generally remain in the phenol product, thereby avoiding the need for expensive separation processes.

It will be understood that the dehydrogenation step disclosed herein may be the sole dehydrogenation step, or may be one step in a series of dehydrogenation steps. The steps may be the same or different. For example, the steps may comprise the same or different: dehydrogenation conditions, conversion of cyclohexanone (e.g., <50%) and/or amount of impurities (e.g., <100 ppm by weight of alkylbenzenes).

Where the dehydrogenation step is conducted as a continuous, rather than a batch, process, the weight hourly space velocity (WHSV) of the feed is typically from about 2 to 50 hr$^{-1}$. To improve catalyst stability and assist in extracting the hydrogen generated in the dehydrogenation reaction, hydrogen may be cofed to the dehydrogenation reaction, typically such that the molar ratio of hydrogen to cyclohexanone in the dehydrogenation feed is about 0:1 to about 20:1.

To assist in reduction of impurities, such as alkylbenzenes and alkylphenols, the feed to the dehydrogenation process preferably also comprises a diluent substantially inert under said dehydrogenation conditions. Suitable diluents comprise phenol or a hydrocarbon, such as at least one of cyclohexane and benzene. Typically, the weight ratio of diluent to cyclohexanone in the feed is from about 1:100 to about 10:1.

The reactor configuration used for the dehydrogenation process generally comprises one or more fixed bed reactors containing the dehydrogenation catalyst. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably the last bed in the series runs at a higher exit temperature than the first bed in the series.

The effluent from the cyclohexanone dehydrogenation reaction is composed mainly of phenol and hydrogen. The desired phenol is easily removed from the reaction effluent by fractionation to leave a hydrogen stream which, after suitable purification, can be recycled to the benzene hydroalkylation step.

By employing the present dehydrogenation process, substantially all the cyclohexanone in the cyclohexylbenzene hydroperoxide cleavage effluent can be converted to phenol. In practice, however, depending on market conditions, there is likely to be a significant demand for cyclohexanone product. This can readily met using the present process by reliance on the reversible nature of the reaction (2), namely by hydrogenating at least some of the phenol back to cyclohexanone. This can readily be achieved by, for example, contacting the phenol with hydrogen in the presence of a hydrogenation catalyst, such as platinum or palladium, under conditions including a temperature of about 20° C. to about 250° C., a pressure of about 101 kPa to about 10000 kPa and a hydrogen to phenol molar ratio of about 1:1 to about 100:1.

The invention will now be more particularly described with reference to the following non-limiting Examples.

In the Examples, a catalyst comprising 1 wt % K and 1 wt % Pt on 1/20" quadrulobe silica extrudate was employed to effect dehydrogenation of various cyclohexanone-containing feeds under various conditions.

The catalyst was prepared by loading 1 wt % K on the silica extrudate by incipient wetness impregnation with a potassium carbonate solution. After K impregnation, the sample was dried in air at 121° C. followed by calcination in air at 538° C. 1 wt % of Pt was then loaded onto the 1% K/SiO2 by incipient wetness impregnation with a tetraamine platinum nitrate solution. The sample was dried at 121° C. following platinum impregnation. The dried sample was then calcined at 350° C. in air and then cut into catalyst particles of L/D (length/diameter) of about one.

400 mg of the resultant catalyst particles were mixed with 1.5 g of 96-160 micron glass microspheres, and the mixture was packed into a 1/4" (0.6 cm) internal diameter, stainless steel downflow reactor. A cyclohexanone-containing feed was delivered to the reactor using an ISCO pump and was vaporized prior to mixing with $H_2$. The reaction was run at temperatures varying between 375° C. and 425° C. and total reactor pressures of 50 to 100 psig (445 to 790 kPa, gauge). The $H_2$/cyclohexanone ratio of the feed was 2:1.

The effluent from the reactor was sampled using a Valco sampling valve, and the sample was sent to an on-line GC equipped with a FID for analysis. All the hydrocarbons were analyzed and the results were normalized. $H_2$ was not included in the analysis. Conversion was calculated based on the concentration of cyclohexanone in the effluent. Cyclohexanol, which was typically present in the effluent, was counted as unreacted feed. The results are summarized in Table 1, where all concentrations shown are in wt %.

Example 1

Cyclohexanone Conversion at 425° C., 100 psig, and 3.75 WHSV with Cyclohexanone Feed Run condition 1 in Table 1 shows yield data for conversion of a cyclohexanone feed at 425° C., 100 psig (790 kPa, gauge), 3.75 WHSV and $H_2$/cyclohexanone molar ratio of 2. At least 9 alkylbenzene and alkylphenol species were identified in the product, namely t-butylbenzene, 2-methyl phenol, 3-methyl phenol, n-butyl benzene, 1-methylbutyl benzene, pentylcyclohexane, n-pentylbenzene, and 1-pentenyl benzene. These species boil close to phenol and so it is difficult to separate them from phenol via conventional fractionation. Note that the concentrations of t-butylbenzene, 2-methylphenol, n-butylbenzene and n-pentyl benzene in the product were measured to be 48.18, 79.40, 68.36, and 61.69 ppm, respectively. The totals of alkylbenzenes/alkylphenols and heavies are 330.59 ppm and 6532.86 ppm, respectively.

Example 2

Cyclohexanone Conversion at 425° C., 100 psig, and 3.75 WHSV with 50% Cyclohexanone/50% Phenol Feed Run condition 2 in Table 1 summarizes the yield data for conversion of a 50% cyclohexanone/50% phenol feed using the same conditions as Example 1. The concentrations of t-butylbenzene, 2-methylphenol, n-butylbenzene and n-pentyl benzene in the product were 36.27, 27.67, 33.31, and 63.32 ppm, respectively. The values are comparable or slightly lower than those Example 1, but still relatively high, suggesting dilution of feed with phenol at this temperature is not very effective in reducing impurities.

Example 3

Cyclohexanone Conversion at 375° C., 100 psig, and 3.75 WHSV with 50% Cyclohexanone/50% Phenol Feed Run condition 3 in Table 1 summarizes the yield data for a 50% cyclohexanone/50% phenol feed at 375° C., 100 psig (790 kPa, gauge), 3.75 WHSV and $H_2$/cyclohexanone molar ratio of 2. The concentrations of t-butylbenzene, 2-methylphenol, n-butylbenzene and n-pentyl benzene in the product were 49.71, 10.04, 0.00, 44.83 ppm, respectively. The values for the later three species are lower than those in Examples 1 and 2, suggesting that lower temperature is favorable in terms of reducing impurities. The total of heavies was 141.98 ppm showing some improvement over that measured at 425° C.

Example 4

Cyclohexanone Conversion at 375° C., 50 psig, and 3.75 WHSV with 50% Cyclohexanone/50% Phenol Feed Run condition 4 in Table 1 summarizes the yield data for a 50% cyclohexanone/50% phenol feed at 375° C., 50 psig (445 kPa, gauge), 3.75 WHSV and $H_2$/cyclohexanone molar ratio of 2. The concentrations of t-butylbenzene, 2-methylphenol, n-butylbenzene and n-pentyl benzene in the product were 25.80, 0.00, 0.00, and 1.15 ppm, respectively. The values are significantly lower than those in Example 1 or completely eliminated, suggesting that low pressure is favorable for reducing or eliminating impurity formation. The totals of alkyl benzenes and heavies were 26.95 ppm and 5512.12 ppm, respectively. Thus the amount of heavies was reduced somewhat, but not as significantly as the alkyl benzenes.

Example 5

Cyclohexanone Conversion at 375° C., 50 psig, and 3.75 WHSV with Cyclohexanone Feed Run condition 5 in Table 1 shows yield data for conversion of a cyclohexanone feed at 375° C., 50 psig (445 kPa, gauge), 3.75 WHSV and $H_2$/cyclohexanone molar ratio of 2. The concentrations of t-butylbenzene, 2-methylphenol, n-butylbenzene and n-pentyl benzene in the product were 25.80, 0.00, 0.00, and 1.15 ppm, respectively. The values are significantly lower than those in Example 1 or completely eliminated, suggesting that low pressure is favorable for reducing or eliminating impurity formation. The yield of heavies (total) was 5512.12 ppm.

Example 6

Cyclohexanone Conversion at 375° C., 50 psig, and 3.75 WHSV with 50% Cyclohexanone/50% Benzene Feed Run condition 6 in Table 1 summarizes the yield data for a 50% cyclohexanone/50% benzene feed at 375° C., 50 psig (445 kPa, gauge), 3.75 WHSV and $H_2$/cyclohexanone molar ratio of 2. Note that the yield of alkylbenzenes and heavies in the product is 48.86 ppm and 3045.72 ppm, respectively, which is a significant improvement over the values measured at 425° C., 100 psig (689 kPa, gauge) with 100% cyclohexanone feed (Example 1).

Example 7

Cyclohexanone Conversion at 425° C., 50 psig, and 3.75 WHSV with 50% Cyclohexanone/50% Benzene Feed Run condition 7 in Table 1 summarizes the yield data for a 50% cyclohexanone/50% benzene feed at 425° C., 50 psig (445 kPa, gauge), 3.75 WHSV and $H_2$/cyclohexanone molar ratio of 2. The yield of alkylbenzenes and heavies in the product is 54.29 ppm and 2768.49 ppm, respectively. Similar to Example 6, the results from this Example 7 are much better than those obtained under the run condition of Example 1. However, an advantage of Example 7 over Example 6 is the much higher phenol yield (40.39 wt % in Example 7 vs. 16.20 wt % in Example 6).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

TABLE 1

| | \multicolumn{9}{c}{Run Conditions} | | | | | | | | |
|---|---|---|---|---|---|---|---|---|---|
| | 1 | 2 | 3 | 4 | 5 | 6 | 7 | 8 | 9 |
| | \multicolumn{9}{c}{Temperature, deg C.} | | | | | | | | |
| | 425 C. | 425 C. | 375 C. | 375 C. | 375 C. | 375 C. | 425 C. | 425 C. | 425 C. |
| | \multicolumn{9}{c}{Pressure, psig} | | | | | | | | |
| | 100 psig | 100 psig | 100 psig | 50 psig | 50 psig | 50 psig | 50 psig | 100 psig | 100 psig |
| | \multicolumn{9}{c}{feed composition, wt %} | | | | | | | | |
| | CHone | 50/50 PhOH/ CHone | 50/50 PhOH/ CHone | 50/50 PhOH/ CHone | CHone | 50/50 Bz/ CHone | 50/50 Bz/ CHone | 50/50 Bz/ CHone | 50/50 PhOH/ CHone |
| | \multicolumn{9}{c}{WHSV, hr−1} | | | | | | | | |
| | 3.75 WHSV ppm | 3.75 WHSV ppm | 3.75 WHSV ppm | 3.75 WHSV ppm | 3.75 WHSV ppm | 3.75 WHSV ppm | 3.75 WHSV ppm | 3.75 WHSV ppm | 3.75 WHSV ppm |
| propane | 32.23 | 14.28 | 0.00 | 0.00 | 0.00 | 0.00 | 0.00 | 7.69 | 2.93 |
| C4 | 50.03 | 20.65 | 0.00 | 0.00 | 0.00 | 0.00 | 0.00 | 6.84 | 2.76 |
| C5 | 35.89 | 7.28 | 0.00 | 0.00 | 0.00 | 0.00 | 0.00 | 0.00 | 0.00 |
| C5-2 | 7451.81 | 3986.60 | 717.90 | 50.16 | 50.16 | 26.80 | 76.83 | 309.79 | 646.53 |
| 2-MP | 245.34 | 173.20 | 16.53 | 5.52 | 5.52 | 0.00 | 15.63 | 31.31 | 55.68 |
| hexane | 11.72 | 2.97 | 0.00 | 0.00 | 0.00 | 0.00 | 0.00 | 5.66 | 2.52 |
| MCP | 106.52 | 94.25 | 41.24 | 6.81 | 6.81 | 98.03 | 111.28 | 182.69 | 101.93 |
| benzene | 64108.88 | 48904.08 | 10833.81 | 7500.75 | 7500.75 | 489607.97 | 499153.61 | 503250.12 | 26824.21 |
| cyclohexane | 4125.68 | 7099.73 | 8922.87 | 6522.71 | 6522.71 | 8779.00 | 3906.54 | 10308.57 | 11056.82 |
| cyclohexene | 78.63 | 82.49 | 193.85 | 1844.94 | 1844.94 | 1918.66 | 1063.78 | 424.45 | 460.87 |
| toluene | 46.97 | 15.91 | 0.00 | 0.00 | 0.00 | 14.92 | 15.82 | 14.68 | 0.00 |
| 2-hexanone | 120.20 | 55.50 | 0.00 | 0.00 | 0.00 | 0.00 | 0.00 | 0.00 | 8.81 |
| 3-hexanone | 0.00 | 0.00 | 0.00 | 0.00 | 0.00 | 0.00 | 0.00 | 0.00 | 0.00 |
| 2-methylcyclopentanone | 1033.78 | 663.11 | 108.89 | 3.68 | 3.68 | 0.00 | 29.01 | 57.75 | 128.32 |
| ethylbenzene | 19.49 | 2.62 | 0.00 | 0.00 | 0.00 | 1.76 | 1.45 | 5.97 | 0.00 |
| cyclohexanol | 10341.61 | 7825.53 | 68006.99 | 27644.86 | 27644.86 | 25459.31 | 7371.33 | 7764.25 | 6470.29 |
| cyclohexanone | 60020.87 | 48351.14 | 205785.88 | 234577.32 | 234577.32 | 308206.75 | 80887.18 | 39687.26 | 54959.07 |
| 2-methyl 2-cyclopenten-1-one | 73.04 | 36.84 | 0.00 | 0.00 | 0.00 | 0.00 | 0.00 | 0.00 | 0.00 |
| 2-cyclohexene-1-one | 545.84 | 471.92 | 543.48 | 654.40 | 654.40 | 715.10 | 599.31 | 276.96 | 477.08 |
| phenol | 844258.40 | 872938.91 | 695755.81 | 715438.98 | 715438.98 | 161961.80 | 403889.31 | 433820.76 | 890045.12 |
| t-butylbenzene | 48.18 | 42.86 | 49.71 | 25.80 | 25.80 | 19.23 | 18.08 | 18.85 | 33.92 |
| 2-methyl phenol | 79.40 | 32.71 | 10.04 | 0.00 | 0.00 | 0.00 | 0.00 | 5.55 | 7.32 |
| 3-methyl phenol | 22.55 | 4.01 | 0.00 | 0.00 | 0.00 | 0.00 | 0.00 | 0.00 | 0.00 |
| n-butyl benzene | 68.36 | 39.36 | 0.00 | 0.00 | 0.00 | 0.00 | 0.00 | 0.00 | 0.00 |
| 1-methylbutyl benzene | 7.43 | 1.51 | 0.00 | 0.00 | 0.00 | 0.00 | 0.00 | 0.00 | 0.00 |
| pentylcyclohexane | 29.50 | 2.56 | 47.44 | 0.00 | 0.00 | 13.90 | 0.00 | 4.16 | 1.79 |
| n-pentyl benzene | 61.69 | 76.01 | 44.83 | 1.15 | 1.15 | 15.73 | 17.69 | 23.29 | 21.77 |
| 1-pentenyl benzene | 7.28 | 0.00 | 0.00 | 0.00 | 0.00 | 0.00 | 0.00 | 0.00 | 0.00 |
| cyclopentyl benzene | 39.66 | 19.12 | 0.00 | 0.00 | 0.00 | 0.00 | 18.52 | 21.05 | 5.80 |
| unknown1 | 68.48 | 27.70 | 0.00 | 0.00 | 0.00 | 0.00 | 0.00 | 1.54 | 0.00 |
| CHB | 26.11 | 74.86 | 329.62 | 210.82 | 210.82 | 115.32 | 48.22 | 96.21 | 218.97 |
| dicyclohexyl ether | 314.85 | 36.79 | 63.21 | 7.72 | 7.72 | 97.84 | 6.85 | 23.48 | 3.55 |
| biphenyl | 544.46 | 920.64 | 127.20 | 75.38 | 75.38 | 43.71 | 76.01 | 122.70 | 297.80 |
| diphenyl ether | 141.11 | 518.55 | 498.92 | 883.70 | 883.70 | 31.19 | 144.05 | 166.95 | 1070.83 |
| 2-butyl cyclohexanone | 36.50 | 0.00 | 125.75 | 52.90 | 52.90 | 73.32 | 0.00 | 0.00 | 0.00 |
| cyclohexyl phenyl ether | 1078.68 | 315.08 | 1334.48 | 1652.26 | 1652.26 | 181.10 | 118.92 | 168.05 | 709.33 |
| 2-phenyl phenol | 1750.98 | 3995.24 | 3049.83 | 1336.89 | 1336.89 | 1064.12 | 1791.24 | 2389.20 | 4533.35 |
| dibenzofuran | 921.97 | 432.96 | 127.32 | 78.25 | 78.25 | 54.00 | 88.35 | 158.24 | 329.60 |
| 2-cyclohexyl phenol | 167.54 | 68.33 | 2469.37 | 1307.42 | 1307.42 | 1500.44 | 499.61 | 515.36 | 837.12 |
| 4-phenyl phenol | 1245.22 | 1841.63 | 203.15 | 0.00 | 0.00 | 0.00 | 34.82 | 66.71 | 149.67 |
| heavies1 | 293.36 | 545.07 | 457.13 | 106.37 | 106.37 | 0.00 | 8.64 | 37.26 | 469.42 |
| heavies2 | 11.07 | 2.72 | 0.00 | 0.00 | 0.00 | 0.00 | 0.00 | 0.00 | 0.00 |
| heavies3 | 5.41 | 34.12 | 134.73 | 11.23 | 11.23 | 0.00 | 0.00 | 0.00 | 56.47 |
| heavies4 | 21.69 | 26.55 | 0.00 | 0.00 | 0.00 | 0.00 | 0.00 | 0.00 | 0.00 |
| heavies5 | 0.00 | 0.00 | 0.00 | 0.00 | 0.00 | 0.00 | 0.00 | 0.00 | 0.00 |
| heavies6 | 0.00 | 54.67 | 0.00 | 0.00 | 0.00 | 0.00 | 0.00 | 0.00 | 0.00 |
| total alkylbenzenes | 330.59 | 209.13 | 141.98 | 26.95 | 26.95 | 48.86 | 54.29 | 68.89 | 63.27 |
| total heavies | 6532.86 | 8792.34 | 8591.10 | 5512.12 | 5512.12 | 3045.72 | 2768.49 | 3647.96 | 8457.13 |

The invention claimed is:

1. A process for the dehydrogenation of cyclohexanone to produce phenol, the process comprising contacting a feed comprising cyclohexanone with a dehydrogenation catalyst under dehydrogenation conditions comprising a temperature of about 250° C. to about 375° C. and a pressure of 0 to about 450 kPa, gauge to firm a dehydrogenation product, wherein:

(i) the contacting step converts 0.1 to 50 wt % of the cyclohexanone in the feed to phenol, and (ii) the dehydrogenation product contains less than 100 ppm by weight of alkylbenzenes.

2. The process of claim 1, wherein from about 15 to about 45 wt % of the cyclohexanone in said feed is converted to phenol.

3. The process of claim 1, wherein the dehydrogenation product contains less than 75 ppm by weight of alkylbenzenes.

4. The process of claim 1, wherein the dehydrogenation product contains less than 50 ppm by weight of alkylbenzenes.

5. The process of claim 1, wherein the feed also comprises a diluent that is substantially inert under said dehydrogenation conditions.

6. The process of claim 5, wherein the weight ratio of diluent to cyclohexanone in said feed is from about 1:100 to about 10:1.

7. The process of claim 5, wherein the diluent comprises phenol or a hydrocarbon.

8. The process of claim 5, wherein the diluent comprises at least one of cyclohexane and benzene.

9. The process of claim 1, wherein the dehydrogenation catalyst comprises (i) a support; (ii) a dehydrogenation component comprising at least one metal or compound thereof selected from Groups 6 to 10 of the Periodic Table of Elements; and (iii) potassium or a potassium compound.

10. The process of claim 9, wherein the inorganic support is selected from the group consisting of silica, a silicate, and an aluminosilicate.

11. The process of claim 9, wherein the inorganic support comprises silica.

12. The process of claim 1, wherein the process is conducted in series including at least a first process and a second process for the dehydrogenation of cyclohexanone to produce phenol.

13. The process of claim 12, wherein the first and second dehydrogenation processes each produces a composition comprising less than 50 wt % of cyclohexanone, based upon the weight of the composition.

14. A process for producing phenol from benzene, the process comprising:
(a) reacting benzene and hydrogen with a hydroalkylation catalyst under hydroalkylation conditions to produce cyclohexylbenzene;
(b) oxidizing cyclohexylbenzene from (a) to produce cyclohexylbenzene hydroperoxide;
(c) converting cyclohexylbenzene hydroperoxide from (b) to produce an effluent stream comprising phenol and cyclohexanone; and
(d) contacting at least a portion of the cyclohexanone from (c) with a dehydrogenation catalyst under dehydrogenation conditions comprising a temperature of about 250° C. to about 375° C. and a pressure of 0 to about 450 kPa, gauge wherein:
(i) the contacting step converts 0.1 to 50 wt % of the cyclohexanone in the feed to phenol; and
(ii) the dehydrogenation product contains less than 100 ppm by weight of alkylbenzenes.

15. The process of claim 14, wherein from about 15 to about 45 wt % of the cyclohexanone in said feed is converted to phenol.

16. The process of claim 14, wherein the dehydrogenation product contains less than 75 ppm by weight of alkylbenzenes.

17. The process of claim 14, wherein the dehydrogenation product contains less than 50 ppm by weight of alkylbenzenes.

18. The process of claim 14, wherein the feed also comprises a diluent that is substantially inert under said dehydrogenation conditions.

19. The process of claim 18, wherein the weight ratio of diluent to cyclohexanone in said feed is from about 1:100 to about 10:1.

20. The process of claim 18, wherein the diluent comprises phenol or a hydrocarbon.

21. The process of claim 18, wherein the diluent comprises at least one of cyclohexane and benzene.

22. The process of claim 14, wherein the dehydrogenation catalyst comprises (i) a support; (ii) a dehydrogenation component comprising at least one metal or compound thereof selected from Groups 6 to 10 of the Periodic Table of Elements; and (iii) potassium or a potassium compound.

23. The process of claim 22, wherein the inorganic support is selected from the group consisting of silica, a silicate, and an aluminosilicate.

* * * * *

UNITED STATES PATENT AND TRADEMARK OFFICE
CERTIFICATE OF CORRECTION

PATENT NO. : 9,029,611 B2
APPLICATION NO. : 13/512796
DATED : May 12, 2015
INVENTOR(S) : Teng Xu et al.

It is certified that error appears in the above-identified patent and that said Letters Patent is hereby corrected as shown below:

IN THE CLAIMS, should read

The invention claimed is:

1. A process for the dehydrogenation of cyclohexanone to produce phenol, the process comprising contacting a feed comprising cyclohexanone with a dehydrogenation catalyst under dehydrogenation conditions comprising a temperature of about 250° C. to about 375° C. and a pressure of 0 to about 450 kPa, gauge to form a dehydrogenation product, wherein:
(i) the contacting step converts 0.1 to 50 wt % of the cyclohexanone in the feed to phenol, and
(ii) the dehydrogenation product contains less than 100 ppm by weight of alkylbenzenes.

Signed and Sealed this
Eighth Day of December, 2015

Michelle K. Lee
*Director of the United States Patent and Trademark Office*